(12) United States Patent
Vasudevan et al.

(10) Patent No.: US 11,141,449 B2
(45) Date of Patent: Oct. 12, 2021

(54) METHOD OF EXTRACTING FLAVONOIDS AND/OR POLYPHENOLS FROM DRIED AND POWDERED CITRUS PEELS, COMPOSITIONS THEREFROM, AND METHODS OF TREATMENT OF DISEASES ASSOCIATED WITH CHRONIC INFLAMMATION

(71) Applicant: Tait Laboratories Inc., Vancouver (CA)

(72) Inventors: Harish Vasudevan, SW Calgary (CA); Andrew Tait, Vancouver (CA)

(73) Assignee: Tait Laboratories Inc., Vancouver (CA)

( * ) Notice: Subject to any disclaimer, the term of this patent is extended or adjusted under 35 U.S.C. 154(b) by 946 days.

(21) Appl. No.: 14/905,724

(22) PCT Filed: Jul. 16, 2014

(86) PCT No.: PCT/CA2014/000599
§ 371 (c)(1),
(2) Date: Jan. 15, 2016

(87) PCT Pub. No.: WO2015/006863
PCT Pub. Date: Jan. 22, 2015

(65) Prior Publication Data
US 2016/0158303 A1    Jun. 9, 2016

Related U.S. Application Data

(60) Provisional application No. 61/846,995, filed on Jul. 16, 2013.

(51) Int. Cl.
| | | |
|---|---|---|
| *A61K 36/00* | (2006.01) | |
| *A61K 36/752* | (2006.01) | |
| *A61K 31/7048* | (2006.01) | |
| *A61K 31/352* | (2006.01) | |
| *A23L 2/52* | (2006.01) | |
| *A23L 2/06* | (2006.01) | |
| *A23L 33/105* | (2016.01) | |
| *A23L 19/00* | (2016.01) | |
| *A61K 31/353* | (2006.01) | |

(52) U.S. Cl.
CPC ............ *A61K 36/752* (2013.01); *A23L 2/06* (2013.01); *A23L 2/52* (2013.01); *A23L 19/01* (2016.08); *A23L 33/105* (2016.08); *A61K 31/352* (2013.01); *A61K 31/353* (2013.01); *A61K 31/7048* (2013.01); *A61K 2236/00* (2013.01)

(58) Field of Classification Search
None
See application file for complete search history.

(56) References Cited

FOREIGN PATENT DOCUMENTS

| JP | 2004305027 A | * 11/2004 |
|---|---|---|
| JP | 2004305027 A | 11/2004 |
| KR | 20120089952 A | 8/2012 |

OTHER PUBLICATIONS

Jeong et al, Effect of heat treatment on the antioxidant activity of extracts from citrus peels. Journal of agricultural and food chemistry, (Jun. 2004 (02) vol. 52, No. 11, pp. 3389-93. (Year: 2004).*
Choi, et al., "Effects of Storage Period and Heat Treatment on Phenolic Compound Composition in Dried Citrus Peels (Chenpi) and Discrimination of Chenpi with Different Storage Periods Through Targeted Metabolomic Study Using HPLC-DAD Analysis," Journal of Pharmaceutical and Biomedical Analysis, vol. 54, epub Oct. 8, 2010 (Oct. 8, 2010) pp. 638-645.
Funaguchi, et al., "Narirutin Inhibits Airway Inflammation in an Allergic Mouse Model," Clinical and Experimental Pharmacology and Physiology, vol. 34, No. 8, 2007, pp. 766-770. (Abstract Only).
Ho, et al., "Investigation of Heat Treating Conditions for Enhancing the Anti-inflammatory Activity of Citrus Fruit (*Citrus reticulata*) Peels," Journal of Agricultural and Food Chemistry, vol. 56, epub Jul. 8, 2008 (Jul. 8, 2008), pp. 766-770.
International Search Report for PCT/CA2014/000599, dated Oct. 20, 2014, 6 pages.
Jain, et al., "Evaluation of antioxidative and anti-inflammatory potential of hesperidin and naringin on the rat air pouch model of inflammation," Inflammation Research, vol. 60, epub Dec. 23, 2010 (Dec. 23, 2010), pp. 483-491. (Abstract Only).
Majumdar, et al., "Solubility, Stability, Physicochemical, Characteristics and In Vitro Ocular Tissue Permeability of Hesperidin: a Natural Bioflavonoid," Pharmaceutical Research, vol. 26, epub Sep. 23, 2008 (Sep. 23, 2008) pp. 1217-1225.
Park, et al., "Enzymatic Modification Enhances the Protective Activity of Citrus Flavonoids Against Alcohol-induced Liver Disease," Food Chemistry, vol. 139, epub Jan. 29, 2013 (Jan. 29, 2013). pages 231-240.
Rotelli, et al., "Comparative study of flavonoids in experimental models of inflammation," Pharmacological Research, vol. 48, No. 6, 2003, pp. 601-606. (Abstract Only).

(Continued)

*Primary Examiner* — Qiuwen Mi
(74) *Attorney, Agent, or Firm* — Honigman LLP; Fernando Alberdi; Jonathan P. O'Brien

(57) ABSTRACT

Improved processes for extracting polyphenols and/or flavonoids from citrus peels are provided that comprise 1) heating a ground peel to form a pre-treated, ground peel; and 2) extracting the compounds of interest from the pre-treated, ground peel using a basic solution of pH greater than 7 and less than 12. Such processes serve to increase the efficiency of extraction of the polyphenols and/or flavonoids. In preferred embodiments, the flavonoids extracted include hesperidin and narirutin. These extracts are useful in the preparation of anti-inflammatory medicaments for the treatment of chronic inflammatory disorders such as inflammatory bowel disease, Crohn's disease, irritable bowel syndrome (IBS), and multiple sclerosis.

18 Claims, 8 Drawing Sheets

(56) References Cited

OTHER PUBLICATIONS

Tripoli, et al., "Citrus flavonoids: Molecular structure, biological activity and nutritional properties: A review," Food Chemistry, vol. 104, No. 2, 2007, pp. 466-479. (Abstract Only).
Xu, et al., "Minerals, Phenolic Compounds, and Antioxidant Capacity of Citrus Peel Extract by Hot Water," Journal of Food Science, vol. 73 (1). Published Oct. 25, 2007 (Oct. 25, 2007) pp. C11-C18.

* cited by examiner

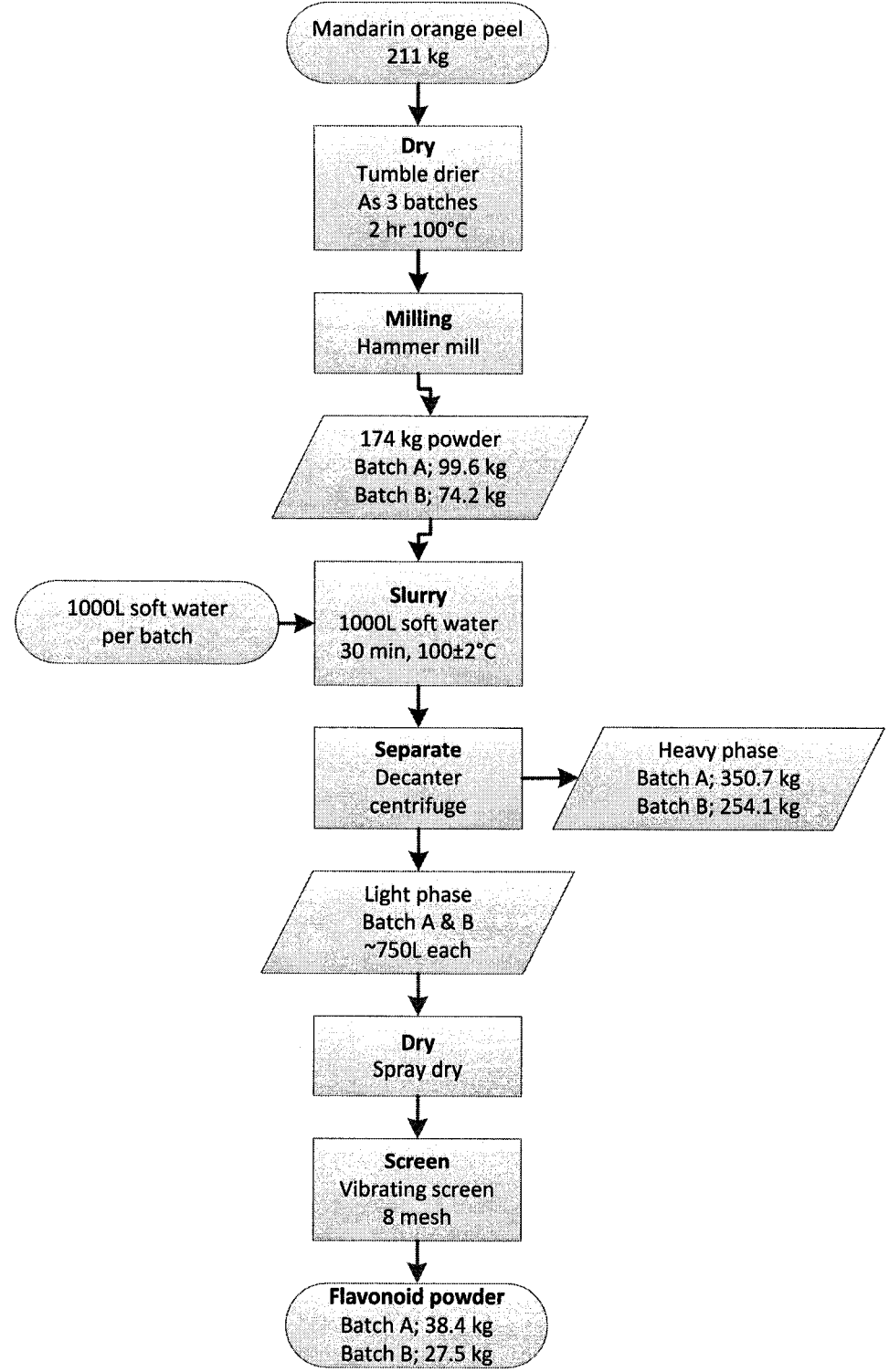
Figure 1 - Flow diagram of the mandarin orange peel process.

Figure 2 - Flavonoid content of five different types of mandarin orange peel.

|  | Bulk (dried) | California | Sino-Nature | Xinhui | Xichuan |
|---|---|---|---|---|---|
| Moisture | 7.68 | 12.5 | 10.9 | 16.2 | 13.6 |
| *Flavonoid (mg/g as is)* | | | | | |
| Narirutin | 15.7 | 9.05 | 11.3 | 3.95 | 3.53 |
| Hesperidin | 68.7 | 40.1 | 64.5 | 83.0 | 96.6 |
| Hesperitin | 0.07 | 0.06 | 0.08 | 0.26 | 0.27 |
| Nobiletin | 0.58 | 0.52 | 0.42 | 11.0 | 7.76 |
| Tangeritin | 0.34 | 0.28 | 0.18 | 8.97 | 3.73 |
| Total | 85.4 | 50.0 | 76.5 | 107.2 | 111.9 |

Figure 3 - Total solids yield and polyphenol content obtained in the different extraction Examples.

| Example | Total solids yield* (%) | Total polyphenol content in extract (% on dwb) |
| --- | --- | --- |
| 1 | 27.3 | 1.34 |
| 2 | 27.7 | 1.38 |
| 3 | 26.0 | 1.24 |
| 4 | 25.4 | 1.33 |
| 5 | 16.4 | 0.81 |
| 6 | 28.8 | 1.2 |
| 6- re-extract | 14.5 | 0.58 |
| 7 | 29.4 | 1.27 |
| 8 | 46.5 | 2.49 |
| 11-Bulk | 44.4 | 2.64 |
| 12-California | 58.0 | 3.61 |
| 13-Sino nature | 53.5 | 3.33 |
| 14- Xinhui | 52.5 | 3.02 |
| 15- Xichuan | 43.5 | 2.44 |

*Yield of dry matter as percentage of the initial peel that was extracted

**Percentage of total polyphenol content on a dry extract basis and expressed as gallic acid equivalents Figure 4 – Flavonoid profiles of bulk orange peels extracted as indicated in Example 11.
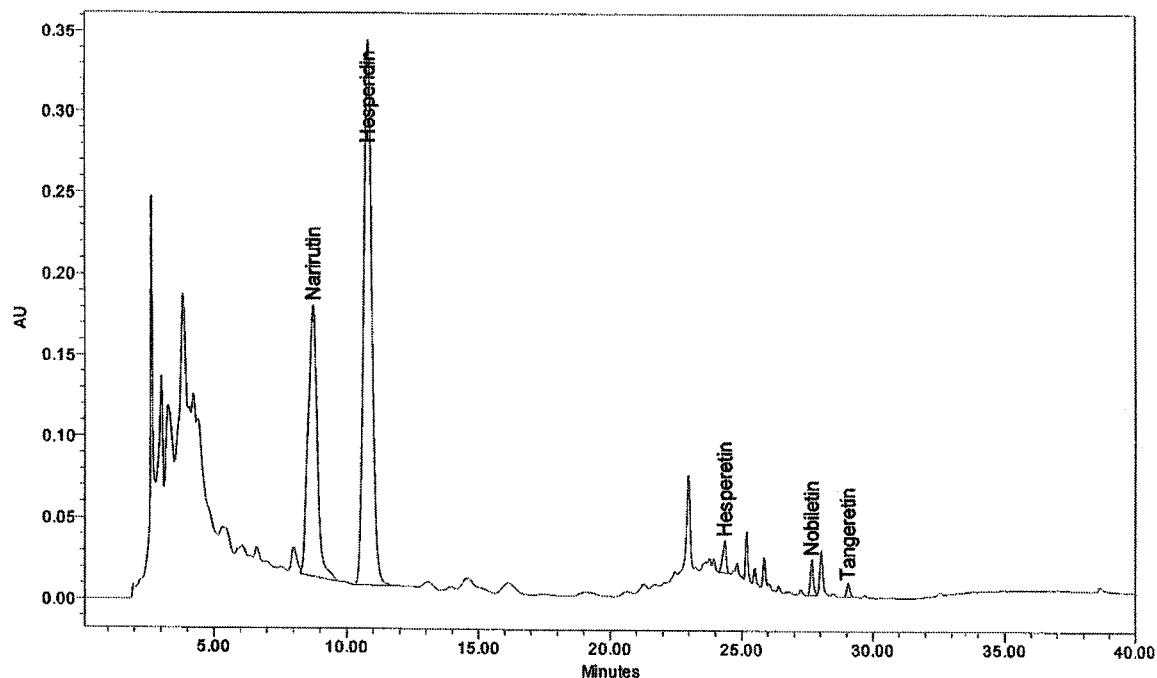

Figure 5 – Flavonoid profiles of California orange peels extracted as indicated in Example 11.
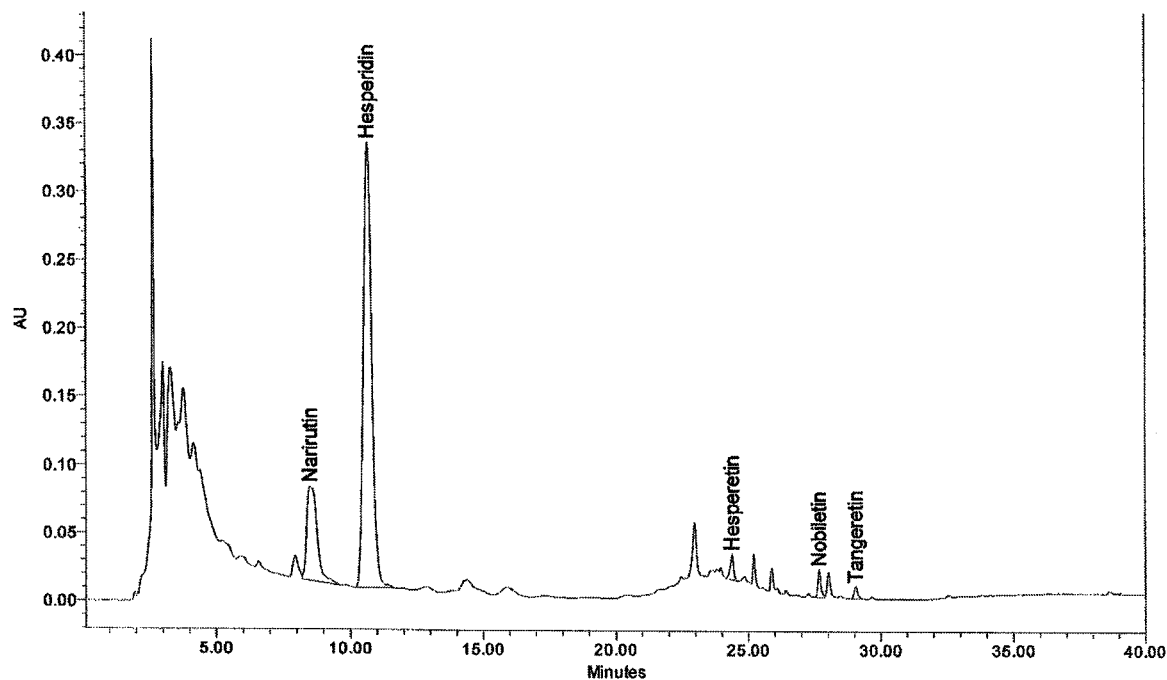

Figure 6 – Flavonoid profiles of Sino-Nature orange peels extracted as indicated in Example 11.
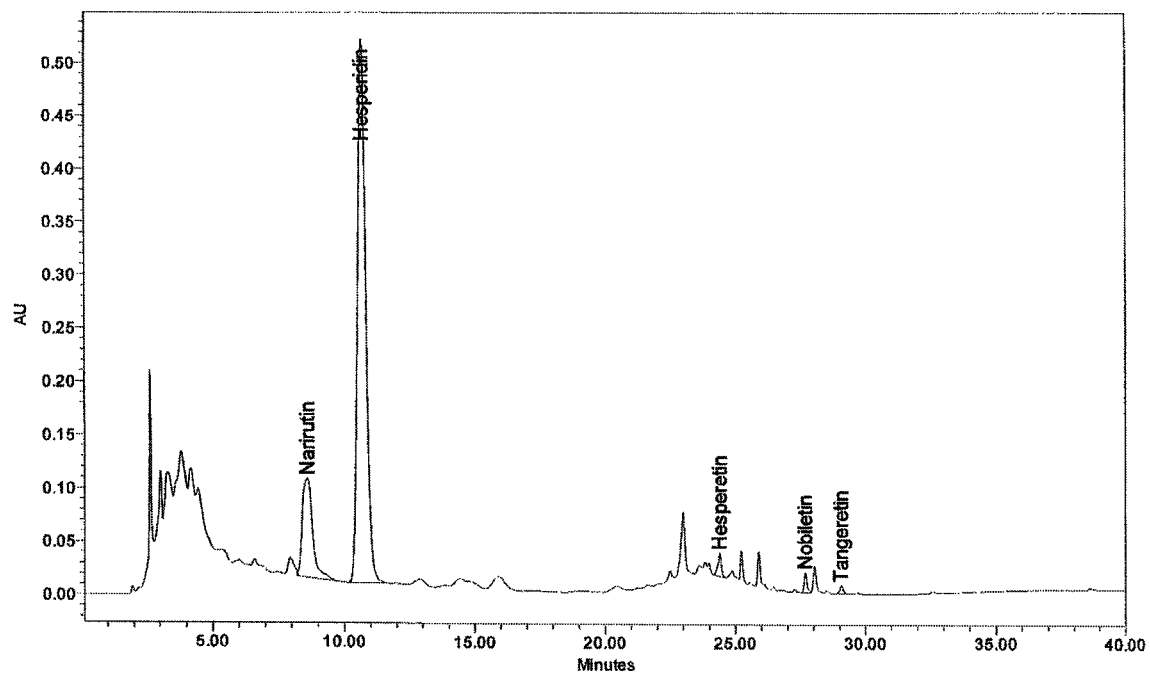

Figure 7 – Flavonoid profiles of XinHui orange peels extracted as indicated in Example 11.
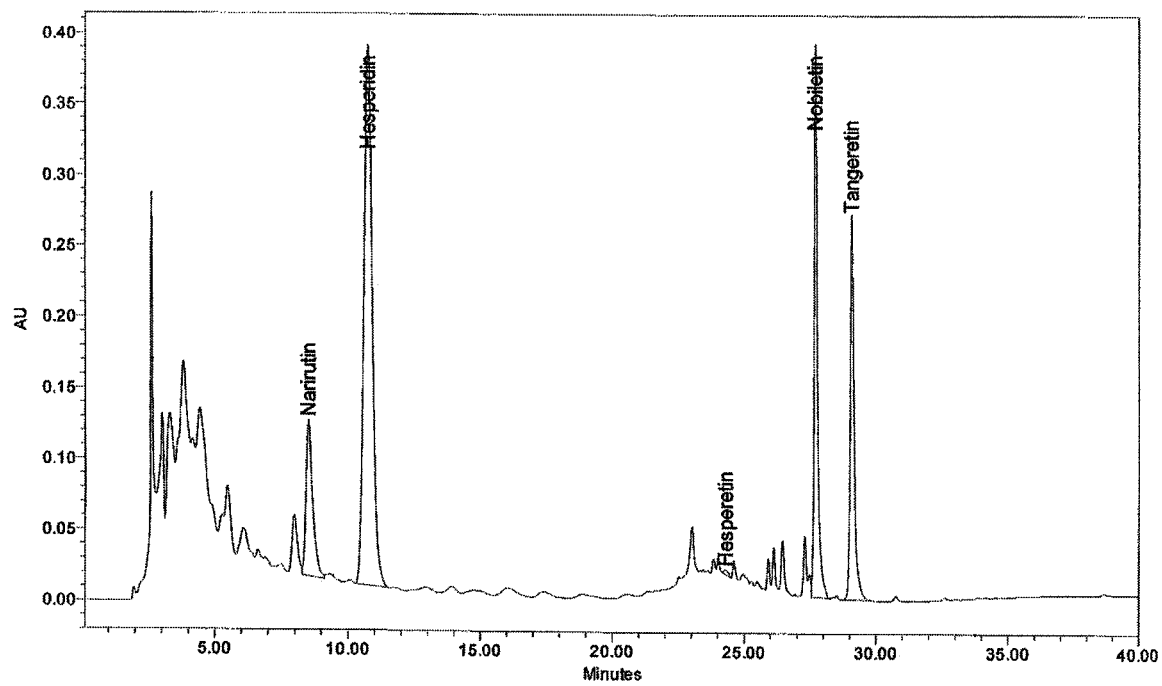

Figure 8 – Flavonoid profiles of Xichuan orange peels extracted as indicated in Example 11.
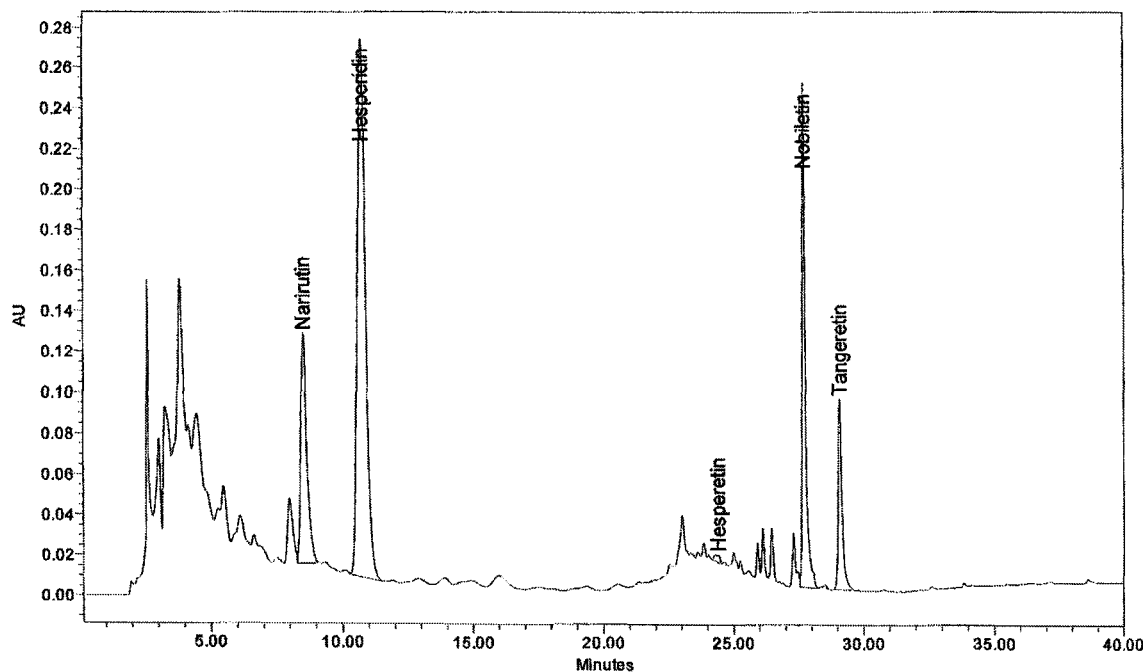

METHOD OF EXTRACTING FLAVONOIDS AND/OR POLYPHENOLS FROM DRIED AND POWDERED CITRUS PEELS, COMPOSITIONS THEREFROM, AND METHODS OF TREATMENT OF DISEASES ASSOCIATED WITH CHRONIC INFLAMMATION

CROSS-REFERENCE TO RELATED APPLICATIONS

This application is a U.S. National Phase of International Application No. PCT/CA2014/000599, filed Jul. 16, 2014, which claims priority to U.S. Provisional Application No. 61/846,995, filed Jul. 16, 2013, the references which are hereby incorporated in their entireties.

FIELD OF THE INVENTION

The present invention relates to the field of natural products for the treatment of inflammation, extracted and purified from citrus peel.

BACKGROUND OF THE INVENTION

Inflammation affects many individuals and is generally an underlying condition in a variety of diseases. Inflammation is a body's defensive response to harmful stimuli used by living organisms to protect damaged areas and assist healing processes. As is known, pathogens, irritants, or damaged cells can trigger the inflammatory response leading to both acute and chronic forms of inflammation. Acute inflammation is generally defined as the body's initial response to harmful stimuli which involves increasing the movement of plasma and leukocytes to the injured area. Chronic inflammation is generally defined as the body's prolonged response to damaged tissue that leads to increased blood flow to and swelling of tissues over longer periods of time.

Despite the contribution of inflammation to healing, a variety of conditions including allergic reactions, atherosclerosis and rheumatoid arthritis can result from the cascade of biochemical events involved in the inflammation process. For example, inflammation can result from exposure to allergens in which a sensitized immune system will initiate antibody production in response to foreign objects. In this case, inflammatory mediators, such as histamine, are released leading to itching, swelling and mucous production. In other examples, atherosclerosis results from chronic inflammation in the walls of arteries leading to plaque formation and arterial narrowing. Rheumatoid arthritis involves an inflammatory response that attacks the synovial joints of an individual leading to pain and disfigurement.

Five types of allergic reactions have been identified. These include: allergy (immediate, Type I), cytotoxic and antibody-dependent (Type II), immune complex mediated (Type III), delayed-type hypersensitivity, cell-mediated immune memory response and antibody-independent (Type IV), and autoimmune disease and receptor mediated (Type V) Immediate or Type I allergic reactions are largely attributed to lgE antibodies, although lgG antibodies can participate in and modulate allergic reactions The allergy is generally caused by the activation of a subpopulation of immune cells, the mast cells and basophils when antigen reacts with lgE antibody receptors on the cell's surface the chemical mediators initiate the allergic reaction by acting on adjacent immune, epithelial, endothelial and smooth muscle cells and promote, in a longer term, the influx of other inflammatory and immune cells (neutrophils, eosinophils, monocytes, lymphocytes) into tissue. This influx of inflammatory cells predisposes the patient to recurrent and sometimes delayed, or prolonged allergic or hypersensitivity reactions. A distinction between immediate and delayed allergic reactions and delayed, chronic immune injury can also be made. The Type 1 allergic reactions are defined according to the location where they occur. Asthmatic reactions occur in the lungs, rhinitis in the nose, conjunctivitis, iritis and uveitis in the eyes, urticara (hives), atopic dermatitis and eczema in the outer skin dermis, angioedema occurs in dermis subcutaneous tissue, mucosa and submucosal tissues. Systemic allergic reactions in the circulatory and in the gastrointestinal system are often life-threatening. Anaphylactic shock, the most severe form of allergy, is a medical emergency. It is often severe and sometimes can provoke a fatal systemic reaction in a susceptible individual upon exposure to a specific antigen (as wasp venom or penicillin) after previous sensitization. Anaphylactic shock is characterized by respiratory symptoms, fainting, itching, urticaria, swelling of the throat or other mucous membranes and a sudden decline in blood pressure. Other symptoms of anaphylactic shock include dizziness, loss of consciousness, laboured breathing, swelling of the tongue, blueness of the skin, bronchospasm, low blood pressure, which in some cases leads to death.

Asthma can be defined clinically as a condition of intermittent, reversible obstruction of the airways, and manifests itself as several clinical entities: allergic asthma, bronchial asthma, exercise induced asthma, chemical induced asthma, and status asthmaticus. Asthma can be divided into two types. Extrinsic asthma is generally triggered by external agents such as allergens (dust mites, pollen, stings, drugs, or foods), and is commonly diagnosed in early life. Intrinsic asthma, which generally develops later in life, can be triggered by congested and inflamed tissues, infection, endogenous catecholamines (e.g. noadrenaline), drugs (e.g. aspirin), stress or exertion. Inflammation can also be triggered by a number of stimuli including heat and chemical burns, exposure to toxins, damaged tissue due to environmental exposure (e.g. frostbite), infections including bacteria, viruses, and parasites, physical injury, immune reactions including allergic reactions and autoimmune conditions, exposure to radiation, as well as the presence of foreign bodies such as splinters or dirt.

Symptoms of inflammation include redness of the affected area, swollen and/or sore joints, stiffness of joints and in some cases even loss of joint function. Fever, chills and fatigue may also be side effects of an inflammatory response in the individual. In addition to these side effects, a number of diseases can result from chronic inflammation including asthma, hay fever, tendonitis, bursitis, arthritis, diabetes, heart disease, atherosclerosis, atopic dermatitis (eczema), contact dermatitis, psoriasis, irritable bowel syndrome, Crohn's disease, colitis, ileitis, gastritis, diverticulitis, ulcerative colitis hepatitis, nephritis, lupus erythematous, Alzheimer's disease, Parkinson's disease and even cancer.

Medically treating inflammation typically involves the use of pharmaceuticals such as non-steroidal and steroidal anti-inflammatory drugs, Non-steroidal anti-inflammatory drugs (NSAIDs) can include over the counter medications such as aspirin, ibuprofen or naproxen. NSAIDs generally work by blocking the cyclooxygenase enzymes responsible for the production of prostaglandins; a group of lipid compounds that promote inflammation. Other pharmaceuticals include methotrexate, sulfasalazine, anti-TNF medications, cydophosphamide and mycophenolate.

Steroidal treatments often involve the use of corticosteroids that act on the immune system to block the production of substances that trigger allergic and inflammatory reactions. Like NSAIDs, corticosteroids inhibit prostaglandin production thereby reducing the normal inflammatory response in the individual.

Immune-selective anti-inflammatory derivatives (imSAIDs) are another class of anti-inflammatory compounds. Generally, imSAIDs are a class of peptides that alter the activation of immune cells (leukocytes) responsible for the inflammatory response.

Natural approaches can also be used to treat inflammation and are gaining increased favour. Herbs such as willow bark, meadowsweet, ginger, ginseng, and licorice, have been shown to exhibit anti-inflammatory properties. Omega-3 fatty acids have also been shown to induce an anti-inflammatory response in addition to vitamins Bi 2, C and E and the minerals copper and zinc.

Nutraceuticals such as probiotics, which are defined as healthy microorganisms living in the intestinal tract of mammals, and prebiotics, the non-digestible food ingredients that stimulate the growth of healthy bacteria, have also shown anti-inflammatory properties. Symbiotics, which combine prebiotics with probiotics, can be used for treating, alleviating and reducing the symptoms associated with inflammation.

These natural alternatives have gained favour for many reasons, including the disadvantages of common NSAID treatments such as adverse effects that may be associated with direct use and/or combinational risk. Both gastrointestinal and renal effects, which can lead to hypertension, are the most common side effects of NSAIDs use. Cardiovascular risk is possible as well as the potential to adversely affect the fetus during pregnancy. Since prostaglandins protect the stomach and assist in blood clotting, NSAIDs can lead to stomach ulcers and promote bleeding.

Furthermore, corticosteroids impede the function of white blood cells which keep the immune system functioning properly. Over time, use of corticosteroids can affect the function of the adrenal glands responsible for the natural production of corticosteroids. They can also increase the risk of high blood pressure and bone diseases such as osteoporosis. Upset stomach and vomiting are common in addition to sleep problems and indigestion. The lowering of an individual's resistance to infection is a risk and prolonged use can lead to organ failure.

The use of prebiotics, probiotics or their combination (symbiotics) run the risk of having their therapeutic effect altered when added to food products. Different preparation process may impart different health effects. As such, their quality can be difficult to guarantee. They may also cause gas and/or bloating due to the activity of the microorganisms.

Although the use of vitamins and minerals is generally regarded as safe, excess usage can lead to adverse side effects. Vitamin C can cause nausea and diarrhea when recommended allowances are exceeded while vitamin E can lead to weakness and fatigue. Vitamin Bi 2 may induce diarrhea and insomnia in certain individuals.

Another natural source of anti-inflammatory compounds is various plant extracts, as described further below.

Multiple Sclerosis

First described in 1868 by Jean-Martin Charcot, multiple sclerosis (MS) is an inflammatory disease in which myelin sheaths around axons of the brain and spinal cord are damaged, leading to loss of myelin and scarring. The name multiple sclerosis refers to scars (sclerae—better known as plaques or lesions) particularly in the white matter of the brain and spinal cord. The cause is not clear, but the underlying mechanism is thought to be either destruction by the immune system or failure of the myelin-producing cells. These changes affect the ability of nerve cells to communicate resulting in a wide range of signs and symptoms. It is more common in women and the onset typically occurs in young adults.[1]

[1] www.wikipedia.com

Almost any neurological symptom can occur, with the disease often resulting in physical and mental difficulties. Psychiatric symptoms may also develop. MS takes several forms, with new symptoms occurring either in discrete attacks (relapsing forms) or accumulating over time (progressive forms). Between attacks, symptoms may go away completely, but permanent neurological problems often occur, especially as the disease advances. Although much is known about the mechanisms involved in the disease process, the cause remains unknown. Proposed causes include genetics and infections. Multiple environmental risk factors have also been reported.

There is no known cure for multiple sclerosis. Treatments attempt to return function after an attack, prevent new attacks, and prevent disability. MS medications can have adverse effects or be poorly tolerated, and many people pursue alternative treatments. About 2 to 150 per 100,000 people are affected.

Myelin Basic Protein's role in MS1

Myelin basic protein (MBP) is a protein believed to be important in the process of myelination of nerves in the nervous system. The myelin sheath is a multi-layered membrane, unique to the nervous system, which functions as an insulator to greatly increase the velocity of axonal impulse conduction. MBP maintains the correct structure of myelin, interacting with the lipids in the myelin membrane.

Interest in MBP has centered on its role in demyelinating diseases, in particular, MS. Several studies have shown a role for antibodies against MBP in the pathogenesis of MS. Some studies have linked a genetic predisposition to MS to the MBP gene.

A "molecular mimicry" hypothesis of multiple sclerosis has been suggested in which T cells are essentially confusing MBP with human herpesvirus-6 (HHV-6). Researchers in the United States created a synthetic peptide with a sequence identical to that of an HHV-6 peptide. They were able to show that T cells were activated by this peptide. These activated T cells also recognized and initiated an immune response against a synthetically created peptide sequence that is identical to part of human MBP. During their research, they found that the levels of these cross-reactive T cells are significantly elevated in multiple sclerosis patients.

Additionally, MBP experiences a rapid turnover of its phosphorylation sites which are a measure of the protein's activity. For example, regulation of phosphorylation in MBP is proposed to have both functional and structural implications for maintaining the efficiency of nerve conduction and physical integrity of the myelin sheath. The amino acid threonine at position 97 (Thr97, of bovine MBP) is an in vivo phosphorylation site recognized by both glycogen synthase kinase (GSK) and MAPK. Phosphorylation at Thr97 attenuates the ability of MBP to polymerize and bundle actin, and to bind actin filaments to a negatively charged lipid membrane. This phosphorylation site has also been proposed to play a role in cell signaling and myelin development.

Due to similarity between MBP and the HHV-6 protein U24, it has been shown in experiments that U24 is able to compete for phosphorylation by kinases, effectively reducing the amount of phosphorylation present on MBP and therefore limiting its activity.[2,3] This in turn has important implications for MS, and establishes the phosphorylation sites of MBP as a target for drug development.

[2] Tait, A. R., Strauss, S. K. (2008) FEBS Letters 582:2685-2688

[3] Sato, N. et. al (2010) eCAM doi: 10.1093/ecam/neq001

Effect of Anti-Oxidant Plant Extracts on Phosphorylation Status of MBP

Ninjin'yoeito (NYT), a Kampo (Japanese traditional) medicine, which is the hot-water extract of a combination of twelve medicinal plants, has long been used for the treatment of various diseases, including dementia and MS in east-Asia. NYT was able to rescue activity of MAPK in an animal model of cuprizone induced neural demyelination, and those same studies also indicated increased levels of MBP phosphorylation and hence activity[4]. Among the ingredients of NYT is mandarin orange peel, known to have significant concentrations of flavonoids and has been shown to be the principal component of NYT that promotes phosphorylation of (myelin basic protein) MBP3.

[4] Seiwa, C. et. al. (2007) eCAM doi:10.1093/ecam/neq001

Mandarin orange peel is often seen in east-Asian traditional medicines, most often dried and powdered and commercially referred to as "chenpi". It is often prescribed in traditional medicine for reducing fevers, asthma, stimulating appetite, and enhancing immune system function[5]. A major component of chenpi are flavonoids and polyphenols in addition to the essential oil rich in D-Limonene which exhibit strong anti-oxidative properties.

[5] Daduo, L. et. al (2011) African Journal of Microbiology Research 5(1): 50-56

Known Flavonoid Extraction Procedures from Chenpi

Typically dried and powdered chenpi is extracted for 45 minutes or longer in a solution of at least 80% ethanol, or alternatively methanol, in a 50:1 ratio of alcohol to chenpi. Following extraction, the sample is centrifuged to remove insoluble material, filtered, and the solution evaporated to provide a final flavonoid rich extract.[6]

[6] Seiwa, C. et. al (2007) Journal of Neuroscience Research 85:954-966

Alternatively, dried and powdered chenpi is extracted in water heated from 40 degrees Celsius to 100 degrees Celsius, at a ratio of 20 parts water to 1 part chenpi for a period of 30 minutes or longer. After allowing the extraction solution to cool to ambient temperature, the solution is centrifuged to remove insoluble material. Insoluble material collected from the centrifugation step can be extracted an additional one or more times, and the further extraction solutions added to the first extraction solution. Typical yields from such water extractions range from 1 milligram (mg) to 5 mg per gram of chenpi extracted[7].

[7] Xu, G. H. et. al (2008) Journal of Food Science 73(1); C11-C18

While there is increasing commercial interest in natural plant products to treat inflammation and other related disorders and conditions, there remain problems and issues with existing products including quality, purity and yield of extracts which limit their overall usefulness and safety and widespread uptake.

It is an object of the present invention to obviate or mitigate some or all of the above noted disadvantages.

SUMMARY OF THE INVENTION

The present invention provides natural anti-inflammatory compositions comprising extracts of citrus peel. The present invention provides natural anti-inflammatory compositions comprising extracts of citrus peel with increased levels of hesperitin and narirutin.

In another aspect, the present invention provides a process of preventing or treating an inflammatory disease in an animal in need of such treatment which comprises administering to said animal a therapeutically effective amount of a composition comprising an extract of citrus peel. The present invention provides a process of preventing or treating an inflammatory disease in an animal in need of such treatment which comprises administering to said animal a therapeutically effective amount of a composition comprising an extract of citrus peel with increased levels of hesperitin and narirutin.

The present invention further provides foods, beverages, nutraceuticals, medicinal formulations, cosmetics, bioceuticals, dietary supplements, health products, condiments and seasonings comprising an extract of citrus peels.

The present invention further provides topical formulations comprising extracts of citrus peel.

In accordance with the invention, there is provided a process of extracting a composition comprising polyphenols and/or flavonoids from citrus peel. The extracted composition can subsequently be used for the treatment of disease associated with chronic inflammation such as, for example, inflammatory bowel disease, Crohn's disease, irritable bowel syndrome, and multiple sclerosis.

In another aspect, the invention provides the use of a therapeutically effective amount of a composition comprising a polyphenol and/or flavonoid extract from citrus peels for treatment of inflammation wherein the use includes oral administration.

The present invention is based in part on an improved process for the extraction of an anti-inflammatory composition from dried and powdered citrus peel (including rinds). The composition, so extracted using the process of the present invention, comprises at least one flavonoid compound and/or at least one polyphenol compound The improved extraction process comprises: 1) heating a ground peel to form a pre-treated, ground peel; and 2) extracting compounds from the pre-treated, ground peel in a solution adjusted to a basic pH, the pH being greater than 7 and less than 12. This process has been found to nearly double the polyphenol and/or flavonoid extraction efficiency due to the key extraction improvements, namely—a heated aqueous extraction at a basic pH, and secondarily due to an earlier heat pre-treatment of the dry ground peel (preferably peel powder) prior to extraction.

It has been surprisingly found that these particular two improvements to known exraction processes yield a highly favourable, therapuetic anti-imflammatory composition.

These and other objects and advantages of the present invention will become more apparent to those skilled in the art upon reviewing the description of the preferred embodiments of the invention, in conjunction with the figures and examples. A person skilled in the art will realize that other embodiments of the invention are possible and that the details of the invention can be modified in a number of respects, all without departing from the inventive concept. Thus, the following drawings, descriptions and examples are to be regarded as illustrative in nature and not limiting.

BRIEF DESCRIPTION OF THE DRAWINGS

Embodiments of the present invention will now be described, by way of example only, with reference to the attached Figures, wherein:

FIG. 1 depicts a flow diagram of the mandarin orange peel process;

FIG. 2-depicts flavonoid content of five different types of mandarin orange peel;

FIG. 3 shows total solids yield and polyphenol content obtained in the different extraction Examples;

FIG. 4 shows flavonoid profiles of bulk orange peels extracted as indicated in Example 11;

FIG. 5 shows flavonoid profiles of California orange peels extracted as indicated in Example 11;

FIG. 6 shows flavonoid profiles of Sino-Nature orange peels extracted as indicated in Example 11;

FIG. 7 shows flavonoid profiles of XinHui orange peels extracted as indicated in Example 11; and FIG. 8 shows flavonoid profiles of Xichuan orange peels extracted as indicated in Example 11.

DETAILED DESCRIPTION OF THE INVENTION

A detailed description of one or more embodiments of the invention is provided below along with accompanying figures that illustrate the principles of the invention. As such this detailed description illustrates the invention by way of example and not by way of limitation.

The description will clearly enable one skilled in the art to make and use the invention, and describes several embodiments, adaptations, variations and alternatives and uses of the invention, including what we presently believe is the best mode for carrying out the invention. It is to be clearly understood that routine variations and adaptations can be made to the invention as described, and such variations and adaptations squarely fall within the spirit and scope of the invention.

In other words, the invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

In the present disclosure and claims (if any), the word "comprising" and its derivatives including "comprises" and "comprise" include each of the stated integers or elements but does not exclude the inclusion of one or more further integers or elements.

As used herein, the term "about" in connection with a measured quantity, refers to the normal variations in that measured quantity, as expected by a skilled artisan making the measurement and exercising a level of care commensurate with the objective of measurement.

As used herein, the singular forms "a," "an," and "the" include plural referents unless the context clearly dictates otherwise. For example, reference to "a substituent" encompasses a single substituent as well as two or more substituents, and the like.

As used herein, the terms "for example," "for instance," "such as," or "including" are meant to introduce examples that further clarify more general subject matter. Unless otherwise specified, these examples are provided only as an aid for understanding the applications illustrated in the present disclosure, and are not meant to be limiting in any fashion.

As used herein, "animal" means any member of the animal kingdom, including preferably humans.

As used herein, "food" or "food product" or "food material" means any safe, ingestible product for animal use, including human use, and includes "functional foods", dietary supplements, nutraceuticals, and "designer foods".

As used herein "natural health products" refer to vvitamins and minerals, herbal remedies, homeopathic medicines, and probiotics As used herein, "functional food" means a product that is similar in appearance to conventional foods that is consumed as part of a usual diet, but which has demonstrated physiological benefits, aside from the pure nutritive advantage.

As used herein, "nutraceutical" means a non-pharmaceutical product prepared in the form of pills, powders, potions and in other medicinal forms not generally associated with food but which has a physiological benefit or provides protection against disease or assists in the treatment of disease or a condition.

As used herein, "bioceutical" refers a healthful compounds or compositions, extracted from natural plants and their derivatives. Anywhere in the world, nutraceuticals, functional foods, natural health products, bioceuticals, and designer foods may be supplemented with or comprise components which provide medical or health benefits, including the prevention and treatment of disease.

As used herein, topical" means the any topical surface of a subject (e.g., patient), such as skin (including under the scalp), nasal, sinus, vaginal, penile, urinary or anal surfaces.

As used herein, treatment" means the management and care of a patient for the purpose of combating an inflammatory disease, disorder or condition. The term is intended to include the alleviation, amelioration or relief of symptoms and complications, and/or the cure or elimination of the disease, disorder or condition.

The terms "therapeutically effective amount" or "effective amount" refers to the amount of composition required in order to achieve the desired therapeutic or cosmetic effects.

As used herein "peel" refers to any citrus peel, preferably orange peel, more preferably mandarin orange peel or tangerine peel, and most preferably "chenpi".

As used herein, the term chenpi or chen pi (pinyin: chénpi) refers to a sun-dried tangerine (mandarin) peel used as a traditional seasoning in Chinese cooking and traditional medicine. Such peels are generally aged by storing them dry.

As used herein, the term "citrus" is meant to include all varieties from the commercially important species, such as Sweet orange (Citrus sinensis), Mandarin and Tangerine (Citrus reticulata), Grapefruit (Citrus paradisi), Lemon (Citrus limon) and Lime (Citrus aurantifolia). Preferred citrus fruits are oranges, including varieties such as Tangerines, Shamouti oranges, Valencia, Blood Oranges, Hamlin, Pera, Navel, Pineapple, Valencia, Salustianas, Blond, Parson Brown, and the like, alone or in combinations.

Citrus fruits, such as oranges, contain compounds called phytochemicals that can be included into three major groups: the flavonoids, limonoids and carotenoids. The flavonoids are a group of benzopyran derivatives which occur widely in plants. The flavonoids typically consist of a benzene ring fused with the heterocyclic six-membered ring containing an oxygen atom. Many flavonoids may also exist as glycosides. The flavonoids in citrus also include the flavone polymethoxylated flavone (in oranges). This compound is represented by flavones substituted by methoxy groups and is unique to citrus. The polymethoxylated flavones have shown cholesterol and lipid lowering potential in animals and possibly humans, and the potential for treating diabetes and inflammation. In citrus fruits, the most predominant flavonoids are the flavanones hesperidin, narirutin and didymin (in oranges).

Process of Extraction and Purification

In accordance with the invention, there is provided a process of extracting an anti-inflammatory composition from citrus peel comprising the step of: grinding citrus peel to form ground peel; drying ground peel prior to extraction and then solubilizing dried peel within a solvent to produce a peel solution, wherein extraction is performed in a solution adjusted to a basic pH, the pH being greater than 7 and less than 12. the key extraction improvements, as described and claimed herein, namely—a heated aqueous extraction at a basic pH, and secondarily due to an earlier heat pre-treatment of the dry peel powder prior to extraction Preferably, pre-extraction drying/heating of ground peel is performed at from 40 degrees Celsius to 200 degrees Celsius, more preferably, 110-130 degrees Celsius, most preferably to about 120 degrees Celsius, for a period of from about 30 minutes to 6 hours. Subsequently, aqueous or solvent extraction is then performed on the dried, ground peel in a solution adjusted to a basic pH, the pH being greater than 7 and less than 12, most preferably the pH being adjusted with sodium hydroxide.

In a preferred embodiment, dry peel powder is heated at 120° C. for 3 hours. This heat treated material is then added to 100° C. soft water (demineralized) in a 1 to 4 to 1 to 50 ratio, most preferably a 1 to 10 ratio (w/w), the pH adjusted to 10 using a 50% sodium hydroxide solution, and the mixture was stirred for 30 min. The resulting aqueous solution will contain an enriched extraction of polyphenols and/or flavonoids. The basic pH is subsequently neutralized by weak acids such as citric acid or ascorbic acid, which will add further beneficial anti-oxidant and health benefits to the solution or a dried powder obtained by evaporation or freeze drying of the solution. Solutions or dried powders can be further processed and packaged using any number of methods commonly employed by those skilled in the art.

Solvent refers to a substance that acts as a dissolving agent or that is capable of dissolving another substance. The most common solvent is water and it is preferred for use herein. Other common solvents which dissolve substances that are insoluble (or nearly insoluble) in water are acetone, alcohol, formic acid, acetic acid, formamide. BTX, carbon disulfide, diemthyl sulfoxide, carbon tetrachloride, chloroform, ether, tetrahydrofuran, furfural, and hexane. They may be classified as polar and non-polar. Polar solvents, like water, have molecules whose electric charges are unequally distributed, leaving one end of each molecule more positive than the other. Usually polar solvent has O—H bond of which water (HOH), methanol ($CH_3OH$) and acetic acid ($CH_3COOH$) are examples. Propanol, butanol, formic acid, formamide are polar solvents. Dipolar solvents which contain a C—O solid bond without O—H bond are acetone [$(CH_3)_2C=O$], ethyl acetate ($CH_3COOCH_2CH_3$), methyl ethyl ketone, acetonitrile, N,N-dimethylformamide and diemthyl sulfoxide. Nonpolar solvents, like carbon tetrachloride ($CCl_4$), benzene ($C_6H_6$), and diethyl ether ($CH_3CH_2OCH_2CH_3$), have molecules whose electric charges are equally distributed and are not miscible with water. Hexane, tetrahydrofuran and methylene chloride are non-polar solvents. Polar solvents are hydrophilic and non-polar solvents are lipophilic. Polar reactants will dissolve in polar solvents. Non-polar solvents dissolve non-polar compounds best. Oil and water don't mix but separate into two layers. There are three measures of the polarity as "dipole moment", "dielectric constant" and "miscibility with water". Though low dipole moments and small dielectric constants indicates non-polar solvents, sharp boundaries between polar and non-polar solvents are not available. The polarity reflects the balance between a polar component (OH) and a non-polar hydrocarbon component, existing in the same molecule. If hydrocarbon character increases relatively, the polarity decreases. On an operational basis, solvents that are miscible with water are polar.

Aqueous solvent may comprise one or more hydrophilic components. Alternatively, the aqueous solvent is hydroselected from the group comprising acetone, alcohol, formic acid, acetic acid, formamide. BTX, carbon disulfide, diemthyl sulfoxide, carbon tetrachloride, chloroform, ether, tetrahydrofuran, furfural, and hexane.

Different types of orange peel used as starting materials were analyzed for their moisture content as well as flavonoid profile according to the traditional method described by the Xu et al[8]. Results are given in FIG. 2, and indicate that there is a great deal of variation in the amount of polyphenols and or flavonoids extracted from orange peels.

[8]Xu, G. H. et. al (2008) Journal of Food Science 73(1): C11-C18

To clarify, the above refers to a methanol-DMSO extract for total content. The enahced flavonoid content of the process of the present invention is illustrated by way of this table:

|  | Flavonoid Yield (%)* | | | | | | |
|---|---|---|---|---|---|---|---|
|  | Trial 2 Bulk | Bulk | California | Sino-Nature | Xinhui | Xu et al Optimal Xichuan conditions- | |
| Narirutin | 34.1 | 37.3 | 52.9 | 55.4 | >100 | >100 | 35.1 |
| Hesperidin | 3.70 | 13.6 | 33.2 | 31.3 | 18.6 | 10.3 | 3.98 |
| Hesperitin | 40.5 | >100 | >100 | >100 | 15.4 | 14.8 | NA |
| Nobiletin | 45.6 | 60.7 | 50.0 | 52.3 | 49.9 | 42.1 | 80 (at low Temp) 32 (at 100° C.) |
| Tangeretin | 29.9 | 34.6 | 39.3 | 44.4 | 37.7 | 29.2 | 56 (at tow Temp) 25 (at 100° C.) |

*Flavonoid yield is expressed as percentage of the particular flavonoid as present in the peel A process to produce a flavonoid rich product from mandarin orange peels is given in FIG. 1. By way of example: a total of 211 kg of peels were dried in the tumble dryer in 3 separate batches. These batches were combined and milled with a hammer mill resulting in 170.8 kg of mandarin orange peel powder. The mandarin orange peel powder was extracted in two batches designated as batch A and batch B. The input for batch A was 99.6 kg of powder and the input for batch B was 74.2 kg. Each batch was extracted in 1000 L of soft water. The extract was recovered from the slurry through centrifugation using a decanter centrifuge at 60° C. The solids obtained were discarded whereas the light phase (extract) was spray dried. In order to minimize losses, the material was not concentrated prior to drying. The solids content, total phenolic content and flavonoid profile of the extract was determined for both batches. Spray drying was conducted at an inlet air temperature of 183±2° C. and a product outlet temperature of 75±5° C. The dried extract was screened through an 8 mesh screen prior to packaging in fiber drums. While spray drying the product, the moisture content was monitored and ranged from 3.6 to 4.2% for batch A and 4.2 to 4.4% for batch B. Material that adhered to the spray dryer wall was collected separately and was not screened. A sample of the screened product from each batch was analyzed for its total phenolic content and flavonoid profile.

It is noted that the sourced two Chinese orange samples, extracted in accordance with the process of present invention, are particularly high in Tangeretin and Hesperidin.

Total polyphenol content was determined using the Folin-Ciocaltieu reagent according to the method for total polyphenols that was originally developed by Slinkard and Singleton and expressed as gallic acid equivalents.

Fifteen different extraction trials were performed and with the exception of the fermentation and enzyme treatment trials, all extracts were analyzed for their total polyphenol content and total solids content. The amount of dry matter extracted given as solids yield as well as the total polyphenol content in these solids are given in FIG. 3.

Total polyphenol content was determined using the Folin-Ciocaltieu reagent according to the method for total polyphenols that was originally developed by Slinkard and Singleton[9] and expressed as a gallic acid equivalents.

[9] Am J Enol Vitic, V 28, No. 1, 1977

The process of the present invention provides a composition in which the amounts of polyphenols and particularly flavonoids are optimized. FIG. 3 indicates that the standard polyphenol and/or flavonoid extraction is 1.38% of the dry weight of aqueous extracted orange peels, as exemplified in Example 2 which is the Xu method8. The optimized polyphenol and/or flavonoid extraction exemplified in Example 11 where polyphenol and/or flavonoid extraction was nearly doubled at 2.64% of the dry weight of aqueous extracted orange peels. Both Examples 2 and 11 used the same type of orange peels from the same batch/lot. The nearly doubling of polyphenol and/or flavonoid extraction efficiency (and the nearly tripling of total ployphenol yield, base dupon the total solids material that can be extratced) is due to the key extraction improvements, as described and claimed herein, namely—a heated aqueous extraction at a basic pH, and secondarily due to an earlier heat pre-treatment of the dry peel powder prior to extraction. The combination of these two improvements results in an optimized protocol. It is believed that either step performed in isolation will not increase yields of polyphenols and/or flavonoids from orange peels.

The dried, concentrated solution or powder of flavonoid and/or polyphenol purified as described can be used to treat diseases and conditions associated with oxidative stress, anti-inflammation, such as age-related joint and tissue degeneration. Specifically the flavonoid and or polyphenol powder can be used to treat neurodegeneration conditions marked by neural demyelination such as multiple sclerosis, where such powder will promote phosphorylation and activation of myelin basic protein, which will in turn provide for re-myelination of neurons.

FIG. 4 illustrates the extracts resulting from the processing of bulk orange peels as indicated in Example 11 that were subsequently analyzed for flavonoid composition by HPLC. The chromatographic method followed was as described in Xu et al[10] using methanol-DMSO as the extraction solvent.

[10] Xu, G. H. et. al (2008) Journal of Food Science 73(1): C11-C18

FIG. 5 illustrates the extracts resulting from the processing of California orange peels as indicated in Example 11 that were subsequently analyzed for flavonoid composition by HPLC. The chromatographic method followed was as described in Xu et al[10] using methanol-DMSO as the extraction solvent.

FIG. 6 illustrates the extracts resulting from the processing of Sino-Nature orange peels as indicated in Example 11 that were subsequently analyzed for flavonoid composition by HPLC. The chromatographic method followed was as described in Xu et al[10] using methanol-DMSO as the extraction solvent.

FIG. 7 illustrates the extracts resulting from the processing of XinHui orange peels as indicated in Example 11 that were subsequently analyzed for flavonoid composition by HPLC. The chromatographic method followed was as described in Xu et al[10] using methanol-DMSO as the extraction solvent.

FIG. 8 illustrates the extracts resulting from the processing of Xichuan orange peels as indicated in Example 11 that were subsequently analyzed for flavonoid composition by HPLC. The chromatographic method followed was as described in Xu et al[10] using methanol-DMSO as the extraction solvent.

Compositions Extracted from Citrus Peel

In certain preferred embodiments, the compositions of the invention as extracted and purified from citrus peel comprise one or more polyphenols and/or flavonoids Preferably, the composition comprises from about 0.4% to about 2% by weight of narirutin, from about 0.2% to about 5% by weight of hesperidin, from about 0.01% to about 1% by weight nobiletin and from about 0.01% to about 1% by weight tangeretin.

What has surprisingly been found is that the compositions are extracted and purified from citrus peel within the process of the present invention have significantly more solubility in water and flowability compared to standard water extracts, not needing carrier agents for the spray drying process in order to maintain integrity of the resulting powder.

In one aspect, the invention provides an anti-inflammatory composition comprising extracts of citrus peel with increased levels of hesperitin and narirutin. The composition may comprise from about 0.4% to about 2% by weight of narirutin, from about 0.2% to about 5% by weight of hesperidin. The composition may comprise from about 0.01% to about 1% by weight nobiletin and from about 0.01% to about 1% by weight tangeretin.

In another aspect, the invention provides a process of preventing or treating disease associated with chronic inflammation. in an animal in need of such treatment which comprises administering to said animal a therapeutically effective amount of a composition comprising an extract of citrus peel with increased levels of hesperitin and narirutin. In the process the extract may comprise from about 0.4% to about 2% by weight of narirutin, from about 0.2% to about 5% by weight of hesperidin. It may comprise from about 0.4% to about 2% by weight of narirutin, from about 0.2% to about 5% by weight of hesperidin and from about 0.01% to about 1% by weight nobiletin and from about 0.01% to about 1% by weight tangeretin. In the process, the disease may be selected from the group consisting of inflammatory bowel disease, Crohn's disease, irritable bowel syndrome, and multiple sclerosis.

In another aspect, the invention provides a use of a therapeutically effective amount of citrus peel extract for treatment of chronic inflammation in an animal, wherein said extract comprises increased levels of hesperitin and narirutin. In the use, the extract may comprise from about 0.4% to about 2% by weight of narirutin, from about 0.2% to about 5% by weight of hesperidin. It may comprise from about 0.4% to about 2% by weight of narirutin, from about 0.2% to about 5% by weight of hesperidin and from about 0.01% to about 1% by weight nobiletin and from about 0.01% to about 1% by weight tangeretin. In the use, the disease may be selected from the group consisting of inflammatory bowel disease, Crohn's disease, irritable bowel syndrome, and multiple sclerosis.

In other aspects, there are food products, beverages, nutraceuticals, pharmaceuticals, and dietary supplements comprising the compositions and extracts decrbied and claimed herein.

In another aspect, the invention provides a process of the extraction of a composition comprising polyphenols and/or flavonoids from citrus peel comprising: a) heating a ground peel to form a pre-treated, ground peel; and 2) extracting compounds from the pre-treated, ground peel in a solution adjusted to a basic pH, the pH being greater than 7 and less than 12.

In another aspect, the invention provides compositions and extracts made of the processes described herein and uses of those compositions and extracts.

Uses of Compositions and Extracts

It is contemplated that the composition of the present invention may be beneficially delivered to animals, including humans for the prevention and/or treatment of inflammatory conditions, diseases and disorders. Such delivery may be systemic administration, such as by a variety of oral dosage forms as described herein.

More specifically, the present invention provides a method for treating or preventing inflammation including chronic inflammation such as inflammatory bowel disease, Crohn's disease, irritable bowel syndrome, multiple sclerosis and diseases and conditions associated with oxidative stress, such as joint and tissue degeneration associated with aging by administering a therapeutically effective amount of the composition as described and claimed herein. More specifically the present invention provides a method for treating or preventing neurodegenerative conditions marked by neural demyelination such as multiple sclerosis, by administering a therapeutically effective amount of the composition described and claimed herein. It is believed that the extracts described herein and forming part of the compositions of the invention, promote phosphorylation and activation of myelin basic protein, which will in turn provide for re-myelination of neurons.

The present invention further provides a method for treating or preventing coronary plaque inflammation, bacterial-induced inflammation, viral induced inflammation and inflammation associated with wounds, acute pain and surgical procedures which comprises administering to an animal, a therapeutically effective amount of the compositions described and claimed herein.

It has surprisingly been found that the extracts and compositions of the present invention exhibit superior anti-inflammatory activity and as such have a wide variety of therapeutic applications. Compositions are administered in amounts which are non-toxic to intended recipient animal.

The desired effects described herein may be achieved in a number of different ways. The compounds and compositions of the present invention may be administered by any conventional means available for use in conjunction with pharmaceuticals, nutraceuticals, foods, beverages, and the like.

A pharmaceutical composition for treating inflammation, as noted herein comprises a citrus peel extract as described herein and an optional adjuvant or carrier.

Dosages

The amount of the compound or composition which is required to achieve the desired therapeutic or cosmetic effects will, of course, depend on a number of factors such as the mode of administration and the condition and size of the animal (subject to be treated). Such dose adaptation is well within the purview of someone skilled in the art.

Dosages of the composition of the invention may vary depending on size and age of the user, and medical conditions, other drugs being taken etc. among other factors, as a directive, traditional medical literature suggests and advocates up to 3-9 gm of dried peel powder, per day. Further, in literature, mice have been shown to tolerate as much as 5 gm/kg dose of mandarin peel extract.

The compounds and compositions of the present invention can be administered:

Within pharmaceutical compositions where they are mixed with suitable carriers or excipients for oral, buccal, or other conventional use.

Mixed within foods

Mixed within beverages

Mixed within nutraceuticals

Mixed within dietary supplements such as vitamins and chewables

Combined as part of bioceutical formulation

Use of physiologically acceptable carriers to formulate the compounds and compositions herein disclosed for the practice of the invention into dosages suitable for systemic administration is within the scope of the invention. With proper choice of carrier and suitable manufacturing practice, the compounds and compositions of the present invention, in particular, those formulated as solutions, may be administered parenterally, such as by intravenous injection. The compounds and compositions can be formulated readily using pharmaceutically acceptable carriers well known in the art into dosages suitable for oral administration. Such carriers enable the compounds and compositions of the invention to be formulated as tablets, pills, capsules (including soft gel capsules), liquids, gels, syrups, slurries, suspensions and the like, for oral ingestion by a patient to be treated.

Pharmaceutical compositions, comprising one or more of the compounds of the present invention, include compositions wherein the active ingredients are contained in an effective amount to achieve their intended purpose. Determination of the effective amounts is well within the capability of those skilled in the art, especially in light of the detailed disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The delivery compositions of the present invention may be manufactured in a manner that is itself known, e.g., by means of conventional mixing, dissolving, granulating, dragee-making, levigating, emulsifying, encapsulating, entrapping or lyophilizing processes.

Formulations for parenteral administration include aqueous solutions of the citrus peel extraction composition in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Preparations for oral use can be obtained by combining the active compositions with solid excipient, optionally grinding a resulting mixture, and processing the mixture of granules, after adding suitable auxiliaries, if desired, to obtain tablets or dragee cores. Suitable excipients include lactose, sucrose, mannitol, sorbitol, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

The compounds and compositions of the present invention may be incorporated directly and without further modification into the food, nutraceutical or beverage by techniques such as mixing, infusion, injection, blending, dispersing, emulsifying, immersion, spraying and kneading. Alternatively, the compounds and compositions may be applied directly onto a food or into a beverage by the consumer prior to ingestion. These are simple and economical modes of delivery.

While the forms of composition, process and process described herein constitute preferred embodiments of this invention, it is to be understood that the invention is not limited to these precise forms. As will be apparent to those skilled in the art, the various embodiments described above can be combined to provide further embodiments. Aspects of the present composition, process and process (including specific components thereof) can be modified, if necessary, to best employ the systems, process, nodes and components and concepts of the invention. These aspects are considered fully within the scope of the invention as claimed. For example, the various process described above may omit some acts, include other acts, and/or execute acts in a different order than set out in the illustrated embodiments.

Further, in the process taught herein, the various acts may be performed in a different order than that illustrated and described. Additionally, the process can omit some acts, and/or employ additional acts.

These and other changes can be made to the present systems, process and articles in light of the above description. In general, in the following claims, the terms used should not be construed to limit the invention to the specific embodiments disclosed in the specification and the claims, but should be construed to include all possible embodiments along with the full scope of equivalents to which such claims are entitled. Accordingly, the invention is not limited by the disclosure, but instead its scope is to be determined entirely by the following claims.

EXAMPLES

Each of the Examples listed started with 50 g of orange peel. For Examples 1 through 11 the bulk peel was used. Examples 12 through 15 consisted of processing the other four mandarin orange peel samples under optimized conditions.

The despite being described as 'dry', the orange peel as a starting material was too moist to mill with a hammer mill, therefore a drying trial was performed to determine a suitable drying temperature and time to obtain a dry peel suitable for milling. The drying trial results indicated that 2.5 hours at 45° C. was sufficient.

As a means to determine the optimized solid to liquid ratio for extraction, the bulk orange peel was mixed at a 1:5 (w/w) and 1:7 of peel and boiling water. The mixtures were stirred for 30 min, followed by wet milling in an Osterizer blender. Both solid to liquid ratios resulted in a thick slurry which could not be properly milled. The optimized solid to liquid ratio was determined to be 1:10.

Example 1

Wet Milling at Higher Solids to Liquid Ratio

Moist bulk peel was mixed with 100° C. soft water at a 1:10 (w/w) peel to water ratio for 30 min, wet milled in the Osterizer blender on high, followed by centrifugation at 3500 rpm for 10 minutes to separate solids from the extract. The extract was analyzed for its solids content as well as total phenols and flavonoid profile.

Example 2

Dry peel at 100° C., 30 Min

Dry peel powder was added to 100° C. soft water in a 1 to 10 ratio (w/w) and the mixture was stirred for 30 min.

After 30 min, the material was centrifuged at 3500 rpm for 10 minutes to recover the liquid and solid phases. The extract was analyzed for total solids content as well as total polyphenols and flavonoid profile.

Example 3

Moist Peel at 80° C., 30 Min

Moist peel was added to 80° C. soft water at a 1 to 10 ratio (w/w) and the mixture was stirred for 30 min. The mixture was wet milled using the Osterizer blender then centrifuged at 3500 rpm for 10 minutes to separate the liquid and solid phases. The extract was analyzed for total solids content as well as total polyphenol content and flavonoid profile.

Example 4

Dry Peel at 80° C., 30 Min

Dry peel powder was added to 80° C. soft water at a 1 to 10 ratio (w/w) and the mixture was stirred for 30 min. The mixture was centrifuged at 3500 rpm for 10 minutes to separate the liquid and solid phases. The extract was analyzed for its total solids content as well as total polyphenol content and flavonoid profile.

Example 5

Percolation 90 Min

Dry peel powder was added extracted using a Soxhlet extractor with 10 parts water at 100° C. for 90 min. The extract was analyzed for its total solids content as well as total polyphenol content and flavonoid profile.

Example 6

Dry Peel at 100° C., 60 Min, Dual Extraction

Dry peel powder was added to 100° C. soft water at a 1 to 10 ratio (w/w) and the mixture was stirred for 60 min. The material was centrifuged at 3500 rpm for 10 minutes and the liquid and solid phases were recovered. The extract was analyzed for its total solids content as well as total polyphenol content and flavonoid profile. The residual solids were extracted a second time under similar conditions and again the total polyphenol content, total solids content and flavonoid profile analyses were performed.

Example 7

Dry Peel at 100° C., 90 Min

Dry peel powder was added to 100° C. soft water at a 1 to 10 ratio (w/w) and the mixture was stirred for 90 min. The material was centrifuged at 3500 rpm for 10 minutes and the liquid and solid phase were recovered. The extract was analyzed for its total solids content as well as total polyphenol content and flavonoid profile.

Example 8

Dry Peel at 100° C. and pH 10, 30 Min

Dry peel powder was added to 100° C. soft water at a 1 to 10 ratio (w/w), the pH was adjusted to 10 using a 50% sodium hydroxide solution and the mixture was stirred for 30 min. The material was centrifuged at 3500 rpm for 10 minutes and the liquid and solid phase were recovered. The extract was analyzed for its total solids content as well as total polyphenol content and flavonoid profile.

Example 9

Fermentation

The dry peel powder was extracted after pretreatment through fermentation. Five g of yeast and 10 g of sucrose were added to 85 mL distilled water and stirred for 20 min at 37° C. Fifty g of this yeast suspension and 50 g of the orange peel powder were added to 450 mL of 37° C. distilled water and the pH was adjusted to 5.5. The slurry was incubated for 24 h while maintaining the pH at 5.5. After the hold was over, a treatment similar to Example 8 was performed: 100° C., extract 30 min, pH 10, followed by centrifugation to separate solids from extract. The extract was analyzed for its total solids content and flavonoid profile.

Example 10

Enzyme Treatment

The peel was extracted after pretreatment through enzymatic digestion. Five g yeast was added to 95 mL of distilled water after which the yeast cell walls were disrupted using a small ball mill-mimicking device (i.e. Swedish tube). Fifty g of this yeast suspension and 50 g of the orange peel powder were added to 450 mL of 40° C. distilled water and the pH was adjusted to 5.5. The slurry was incubated for 24 h while maintaining the pH at 5.5. After the hold was over, a treatment similar to described in Example 8 was performed: 100° C., extract 30 min, pH 10, followed by centrifugation to separate solids from extract. The extract was analyzed for its total solids content and flavonoid profile.

Example 11

Heat Pre-Treatment of Peel

Dry peel powder (50 g) was heated at 120° C. for 3 hours. This heat treated material was added to 100° C. soft water in a 1 to 10 ratio (w/w), the pH was adjusted to 10 using a 50% sodium hydroxide solution and the mixture was stirred for 30 min. The material was centrifuged at 3500 rpm for 10 minutes and the liquid and solid phases were recovered. The extract was analyzed for its total solids content as well as total polyphenol content and flavonoid profile.

Example 12

California Peel

California peel was ground to a powder using a coffee grinder and the resulting powder (50 g) was heated at 120° C. for 3 hours. This heat treated material was added to 100° C. soft water in a 1 to 10 ratio (w/w), the pH was adjusted to 10 using a 50% sodium hydroxide solution and the mixture was stirred for 30 min. The material was centrifuged at 3500 rpm for 10 minutes and the liquid and solid phase were recovered. The extract was analyzed for its total solids content as well as total polyphenol content and flavonoid profile.

Example 13

Sino-Nature Peel

Sino-Nature peel was ground to a powder using a coffee grinder and the resulting powder (50 g) was heated at 120° C. for 3 hours. This heat treated material was added to 100° C. soft water at a 1 to 10 ratio (w/w), the pH was adjusted to 10 using a 50% sodium hydroxide solution and the mixture was stirred for 30 min. After 30 min, the material was centrifuged at 3500 rpm for 10 minutes and the liquid and solid phases were recovered. The extract was analyzed for its total solids content as well as total polyphenol content and flavonoid profile.

Example 14

Xinhui Peel

Xinhui peel was ground to a powder using a coffee grinder and the resulting powder (50 g) was heated at 120° C. for 3 hours. This heat treated material was added to 100° C. soft water at a 1 to 10 ratio (w/w), the pH was adjusted to 10 using a 50% sodium hydroxide solution and the mixture was stirred for 30 min. The material was centrifuged at 3500 rpm for 10 minutes and the liquid and solid phase were recovered. The extract was analyzed for its solids content as well as total polyphenol content and flavonoid profile.

Example 15

Xichuan Peel

Xichuan peel was ground to a powder using a coffee grinder and the resulting powder (50 g) was heated at 120° C. for 3 hours. This heat treated material was added to 100° C. soft water at a 1 to 10 ratio (w/w), the pH was adjusted to 10 using a 50% sodium hydroxide solution and the mixture was stirred for 30 min. After 30 min, the material was centrifuged at 3500 rpm for 10 minutes and the liquid and solid phase were recovered. The extract was analyzed for its total solids content as well as total polyphenol content and flavonoid profile

The invention claimed is:

1. A process of extracting a composition comprising polyphenols and/or flavonoids compounds from citrus peel comprising:
   a) heating a ground citrus peel to a temperature ranging from 100° C. to 130° C. to form a pre-treated, dry ground citrus peel;
   b) solubilizing the pre-treated, dry ground citrus peel in a liquid solution consisting of demineralized water and a base adjusted to a basic pH, the pH being greater than 7 and less than 12, thereby forming a peel solution; and
   c) extracting the polyphenols and/or flavonoids compounds from the peel solution.

2. The process of claim 1 wherein heating at step a) is performed at from 110-130° C.

3. The process of claim 1 wherein heating at step a) is performed from 100 to 120° C.

4. The process of claim 1 wherein heating at step a) is performed from about 30 minutes to 6 hours.

5. The process of claim 1 wherein heating at step a) is performed at 120° C.

6. The process of claim 1 wherein heating at step a) is performed at 100° C.

7. The process of claim 1 wherein at step b) the pH of the demineralized water solution is adjusted with a strong base.

8. The process of claim 1 wherein at step b) the pH of the demineralized water solution is adjusted with a weak base.

9. The process of claim 1 wherein at step b) the pH of the demineralized water solution is adjusted with sodium hydroxide.

10. The process of claim 1 wherein the pH is adjusted to 10.

11. The process of claim 1 wherein the demineralized water solution is heated to 100° C. and the pH is adjusted to 10.

12. The process of claim 1 wherein the pH is adjusted to 10 using a 50% sodium hydroxide solution.

13. The process of claim 1 wherein the pH is adjusted to a pH being greater than 7 and less than 12 using a sodium hydroxide solution.

14. The process of claim 1 wherein at step b) the pre-treated, dry ground citrus peel is solubilized in a demineralized water solution, wherein ratio (w/w) of pre-treated, dry ground citrus peel to solution is 1 to 4 to 1 to 50.

15. The process of claim 1 wherein at step b) the pre-treated, dry ground citrus peel is solubilized in a demineralized water solution, wherein ratio (w/w) of pre-treated, dry ground citrus peel to solution is 1 to 10.

16. The process of claim 1 wherein at step b) the pH of the demineralized water solution is adjusted with a 50% sodium hydroxide solution.

17. The process of claim 1 wherein at step b) after the pH of the demineralized water solution is adjusted, it is mixed and at step c) compounds, including polyphenols and/or flavonoids are extracted from the peel solution by phase separation.

18. The process of claim 1 wherein the citrus peel is orange peel.

* * * * *